US011622683B2

(12) United States Patent
Neice

(10) Patent No.: US 11,622,683 B2
(45) Date of Patent: Apr. 11, 2023

(54) PUPILLOMETRY SYSTEMS, METHODS, AND DEVICES

(71) Applicant: Andrew Elliott Neice, Lake Oswego, OR (US)

(72) Inventor: Andrew Elliott Neice, Lake Oswego, OR (US)

( * ) Notice: Subject to any disclaimer, the term of this patent is extended or adjusted under 35 U.S.C. 154(b) by 225 days.

(21) Appl. No.: 16/865,676

(22) Filed: May 4, 2020

(65) Prior Publication Data

US 2021/0000339 A1    Jan. 7, 2021

Related U.S. Application Data

(60) Provisional application No. 62/922,639, filed on Aug. 20, 2019, provisional application No. 62/921,702, filed on Jul. 2, 2019.

(51) Int. Cl.
| | |
|---|---|
| *A61B 3/00* | (2006.01) |
| *A61B 3/11* | (2006.01) |
| *G06T 7/00* | (2017.01) |
| *A61B 3/14* | (2006.01) |

(52) U.S. Cl.
CPC ............ *A61B 3/112* (2013.01); *A61B 3/0025* (2013.01); *A61B 3/14* (2013.01); *G06T 7/0012* (2013.01); *A61B 2560/0223* (2013.01); *A61B 2560/0247* (2013.01); *G06T 2207/10152* (2013.01); *G06T 2207/30041* (2013.01)

(58) Field of Classification Search
CPC .... A61B 3/00; H04N 7/00; G06T 7/00; G06T 2207/00
See application file for complete search history.

(56) References Cited

U.S. PATENT DOCUMENTS

| | | | | |
|---|---|---|---|---|
| 2012/0287255 | A1* | 11/2012 | Ignatovich | ............. A61B 3/113 348/78 |
| 2016/0192837 | A1* | 7/2016 | Neice | ..................... A61B 3/145 351/206 |

* cited by examiner

*Primary Examiner* — Maryam A Nasri
(74) *Attorney, Agent, or Firm* — Mohr IP Law Solutions, PC

(57) ABSTRACT

Pupillometry systems for measuring pupillary characteristics of a patient are shown and described. The pupillometry systems include at least one camera, and a computer system in data communication with the at least one camera, the computer system having a processor and a non-transitory computer-readable storage medium. The non-transitory computer-readable storage medium includes computer-readable instructions for collecting and time stamping the image data, processing the raw image data in such a way as to bring the images into conformance with standardized image parameters, identifying and measuring the one or more pupils in the image data, processing the image data to produce measurement data of change in the one or more pupillary characteristics, calculating a standardized output of measurement data for the one or more pupillary characteristics, and providing a mechanism to share or store this information with other users via a computer network.

10 Claims, 6 Drawing Sheets

200

302 — USER POSITIONS RADIATION SOURCE AND CAMERA TO PROJECT RADIATION AND CAPTURE IMAGE DATA OF PATIENT'S PUPILS. USER INITIATES CAPTURE

304 — PUPILLOMETRY SYSTEM IDENTIFIES TYPE OF CAMERA AND RADIATION SOURCE AND ADJUST PARAMETERS FOR CAMERA IMAGING, RADIATION SOURCE, OR PUPIL IDENTIFICATION

306 — PUPILLOMETRY SYSTEM LOADS THE RESULTS OF PREVIOUS CALIBRATION AND ADJUSTS PARAMETERS FOR CAMERA IMAGING, RADIATION SOURCE, OR PUPIL IDENTIFICATION

308 — PUPILLOMETRY SYSTEM MEASURES AMBIENT LIGHTING AND ADJUSTS PARAMETERS FOR CAMERA IMAGING, RADIATION SOURCE, OR PUPIL IDENTIFICATION

310 — PUPILLOMETRY SYSTEM IDENTIFIES ITS GEOGRAPHIC LOCATION AND ADJUSTS PARAMETERS FOR CAMERA IMAGING, RADIATION SOURCE, PUPIL IDENTIFICATION, OR PUPIL DATA PROCESSING

312 — BEGIN DATA CAPTURE

FIG. 3

PUPILLOMETRY SYSTEMS, METHODS, AND DEVICES

CROSS REFERENCE TO RELATED APPLICATIONS

This application claims priority to and the benefit under 35 U.S.C. .sctn.119(e) of U.S. Provisional patent application Ser. No. 62/921,702 and 62/922,639, which are hereby incorporated by reference for all purposes.

BACKGROUND

The present disclosure relates generally to pupillometry systems, methods, and devices. In particular, pupillometry systems and methods that automatically reference and incorporate external data in order to improve the quality and utility of pupillometric measurements, and allow communication with other pupillometers in order to streamline medical care.

Changes in the pupil can occur as a result of medications, drugs, and/or toxins (e.g., cough and cold medications, anticholinergic drugs, benzodiazepines, amphetamines, cocaine, lysergic acid diethylamide, marijuana, other narcotics, poisonous mushrooms, belladonna, chloroform, etc.). Pupil changes caused by medications, drugs and toxins are generally temporary. In addition to causing changes in size and response, drugs and/or toxins may affect a characteristic known as pupillary unrest, which is the variation in pupil size about its mean. Determining pupil size, pupillary unrest, pupillary response, and/or other pupillary characteristics can be useful in determining the presence and/or type of medications drugs, and/or toxins in the system of a patient. Further, changes in pupil size and unequal pupil size can be indicators of other serious conditions such as head trauma, brain tumors, and/or stroke. Thus, measuring pupil size and responses can be important for appropriate treatment for a patient.

Devices that measure the radius, diameter, circumference, or other characteristics of a pupil are generally referred to as pupillometers, and the analysis of these measurements is referred to as pupillometry. Pupillometry has a wide variety of applications. For example, precise measurements of pupil size may be useful in planning surgery or other procedures on the eye. Abnormal changes in pupil size, or failure of pupil size to change in response to stimuli (i.e., fixed pupils) may indicate that the patient has a neurological injury. Changes in the pupil size with time (i.e., pupillary unrest) can be correlated with drowsiness. It may additionally correlate with consumption of certain pharmaceuticals, and pupillary unrest may be useful in determining the activity of these pharmaceuticals.

Examples of known pupillometers include pupillometers that use custom designed and configured cameras, lighting, image processing computing devices, displays and housings in order to capture and process images of the pupil. These pupillometers are single-purpose devices. Because these pupillometers tightly control all parameters of image capture they are able to assume constant lighting and capture conditions for any set of pupillographic data, and thus process this data in an identical way without modification.

Another approach uses a general purpose computing device coordinated with a general purpose image capture device, display screen, lighting, and possibly networking and other general purpose electronic or computing equipment. These pupillometers replicate the functions of pupillometers that rely on custom designed hardware but additionally have many of the capabilities and advantages of general purpose devices, and are frequently less costly. Pupillometers of this type have been deployed on a variety of platforms, including desktop computers paired with conventional cameras and lighting, as well as smartphone platforms. The invention described herein is one of the latter types of pupillometer.

Known pupillometers of the latter type are not entirely satisfactory for the range of applications in which they are employed. For example, because they rely on a heterogenous set of cameras and lights in order to capture an image of the pupil, there may be variability in image properties such as color saturation and contrast that are not accounted for by existing pupillometers and may affect the accuracy of the assessment of pupil size. Furthermore the image capture rate may vary depending upon the camera and the capacity of the general purpose computing platform that it interfaces with. The measurement of particular pupillary indices of change, such as pupillary unrest or constriction velocity, may require a particular frame rate or may require adjustment based on frame rate.

Lastly, because these pupillometers do not necessarily integrate with a shroud or other protective covering of the eye, ambient lighting conditions may affect the total amount of light that enters the pupil as well as affecting the lighting conditions of the camera. This variability in measurement conditions can lead to misleading or inaccurate measurements of pupil size or pupillary indices such as pupillary unrest, constriction velocity, or dilation velocity.

Furthermore, because of their known reduced accuracy, pupillometers of the second type are known to frequently identify the pupil in such a grossly erroneous way that the typical user of the pupillometer can clearly identify that the device has malfunctioned. Often, when a series of images of the pupil are captured, the pupillometer will correctly identify the pupil for the majority of the capture, but mis-identify the pupil in several places, rendering the entire capture useless. However, no existing pupillometers allow the user to correct this data or to instruct the pupillometer to ignore this data when calculating pupillary indices such as pupillary unrest, constriction velocity, or dilation velocity.

Thus, pupillometers of the second type are generally considered to be inferior in accuracy to those of the first type, and there exists a need for pupillometry systems, methods, and devices that improve upon and advance the design of known pupillometers. Examples of new and useful pupillometry systems, methods, and devices relevant to the needs existing in the field are discussed below.

Furthermore, pupillometers of both the first and second type also have a variety of shortcomings that limit their utility in providing clinical care. While current pupillometers are able to store pupillographic data, this data is stored locally on the pupillometer. Thus if a healthcare practitioner wishes to follow the pupillographic data of a patient through time, they must have access to the same pupillometer that their previous scans were taken with. Some current pupillometers are able to transmit data to a remote device such as a laptop computer for further analysis, however this practice is limited due to the lack of a central repository for scans that is accessed by all users. Furthermore, current pupillometers are impractical for large-scale sharing of pupillographic data because of lack of security controls regarding which users are allowed to which scans, and an inability to tag each scan with a unique identifier. In order to conform with regulations regarding patient safety and privacy, scans must be stored with a unique patient identifier and access to patient data must be limited to clinicians who have appropriate authorization. Current pupillometers do not have either of these capabilities. Lastly, different pupillometers may have different capture properties and/or data formats, and there is no mechanism for practitioners to easily share or compare pupillographic data that was taken with different pupillometers, or any mechanism by which capture properties can be standardized across an institution.

Furthermore, existing pupillometers do not have the capability to link their operation with the geographic location of the pupillometer. For example, it may be desirable to only allow the pupillometer to operate within the geographic location of a hospital or healthcare facility, in order to prevent unauthorized access of patient data outside the hospital. Alternatively, it may also be desirable to associate particular scans with particular locations, such as a patient room number, in order to avoid storing identifying patient information or to allow for easy identification of patient data. Lastly, particular institutions may have standardized protocols regarding capture of patient data that are associated with particular geographic locations, pupillometers that have the ability to identify their geographic location have the ability to automatically load standardized protocols.

Thus there exists a need for pupillometry systems, methods, and devices that address the inability of current pupillometers to share data in a secure and convenient way between authorized providers. Examples of new and useful pupillometry systems, methods, and devices relevant to addressing these shortcomings are discussed below.

Disclosure addressing one or more of the identified existing needs is provided in the detailed description below. Examples of references relevant to pupillometers include U.S. Patent References: U.S. Pat. Nos. 7,083,280, 9,414, 745, 3,782,364, 5,784,145, 7,625,087, and 8,127,882. The complete disclosures of the above patents are herein incorporated by reference for all purposes.

SUMMARY

The present disclosure is directed to pupillometry systems for measuring one or more pupillary characteristics of a patient. The puillometry systems include at least one camera for capturing image data of one or more pupils, at least one radiation source configured to project radiation to the one or more pupils, and a computer system in data communication with the at least one camera, the computer system having a processor and a non-transitory computer-readable storage medium. The non-transitory computer-readable storage medium includes computer-readable instructions for collecting and time stamping the image data, identifying and measuring the one or more pupils in the image data, processing the image data to produce measurement data of change in the one or more pupillary characteristics, and calculating a standardized output of measurement data for the one or more pupillary characteristics. The non-transitory computer-readable storage medium additionally includes computer-readable instructions for one or more of the following adjusting the parameters used to identify the pupil based on known properties of the imaging device or analysis of images obtained from the imaging device, including, but not limited to, image brightness, contrast, frame rate, magnification, distribution of pixel intensities in one or more color channels adjusting the intensity of the radiation source based on the results of a user calibration, the procedure for which is specified as computer-readable instructions in the non-transitory computer-readable storage medium adjusting the brightness, contrast, zoom, focus, and other camera properties based on the results of a user calibration, the procedure for which is specified as computer-readable instructions in the non-transitory computer-readable storage medium adjusting the intensity of the radiation source based on internally stored data that enumerates recommended values for different types of radiation sources adjusting the brightness, contrast, zoom, focus, and other camera properties based on internally stored data that enumerates recommended values for different types of cameras The purpose of the above listed adjustments may be to increase the accuracy of the identification of the pupil and/or iris by the pupillometer, or to bring the measurements into conformance with captures made by devices with different types of cameras or radiation sources or ambient light conditions, or both.

It will be understood by those skilled in the art that the identification of the camera and the radiation source may be performed by direct or indirect methods. For example, if the pupillometer takes the form of an integrated electronic device with standardized parts, such as a smartphone, the pupillomety system may simply identify the make and model of smartphone and use this information to determine the type of camera and radiation source that it uses. In some cases, the system may make available an application programming interface in order to allow the camera configuration to be changed easily. In other embodiments, the user may be asked to manually enter the camera type, or select it from a list.

Furthermore, the non-transitory computer-readable storage medium may additionally includes computer-readable instructions for one or more of the following allowing the user to inspect the results of the pupil identification procedure and mark certain pieces of data as invalid, either to ignore these pieces, enter replacement data, or reattempt identification of the pupil allowing the user to uniquely label the results of a capture of the image of the pupil, and send and receive sets of pupillary data with other computing devices, including a centralized computing device that is accessed by multiple users allowing the user to limit the ability to capture or view pupil data based on geographic location, or to adjust capture parameters based on geographic data

BRIEF DESCRIPTION OF THE DRAWINGS

FIG. 3 is a flow diagram of a first example method of the first example pupillometry system shown in FIG. 2, prior to beginning data capture.

DETAILED DESCRIPTION

Figure 1:
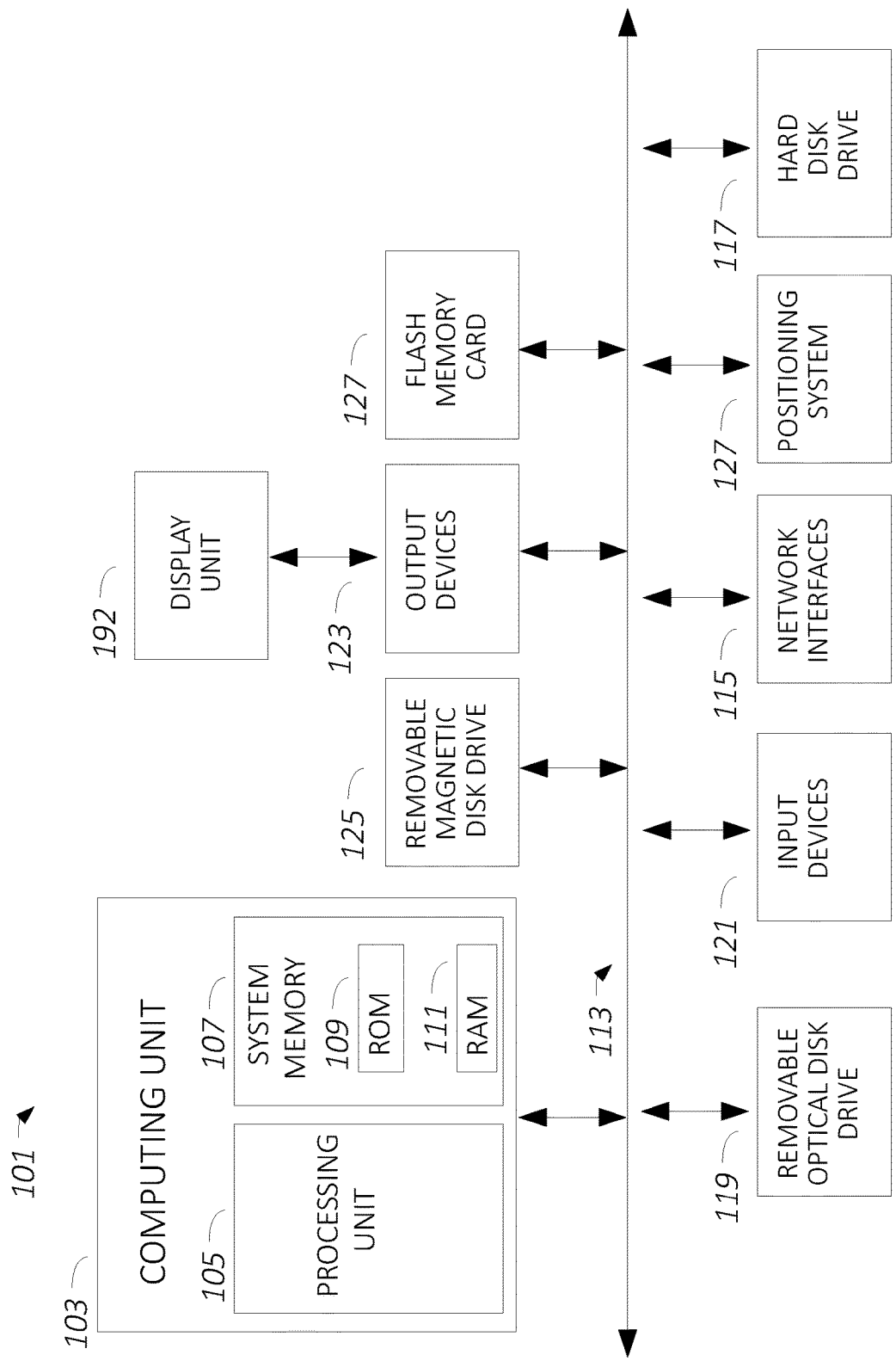
FIG. 1 is a schematic view of an example of a programmable computing device.

The disclosed pupillometry systems, methods, and devices become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various pupillometry systems, methods, and devices are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

With reference to FIGS. 1-6, a first example of an enhanced pupillometry system, system 200, will now be described. Like existing pupillometry systems, pupillometry system 200 allows for an operator 202 to collect and analyze pupillometry data collected from a patient 204. Specifically, pupillometry system 200 functions to collect, process, and analyze puillometry data from patient 204 and display a standardized output of pupillometry data to operator 202. Additionally or alternatively, system 200 can be used to diagnose the patient or determine the presence and/or type of medications, drugs, or toxins that may have been consumed by the patient.

Like existing pupillometry systems, System 200 includes a computer system 206 having at least a non-transitory computer-readable storage medium 208, a processor 210, and a display 212. System 200 further includes a positioning device 214 for positioning a radiation source 216 and a camera 218 in a position to project light into and capture image data from one or more of the pupils of the patient. In the preferred embodiment of the pupillometry system, system 200 further includes a communication device 220 to transmit and receive data with a remote computer system 222 as well as a positioning system 224 that is able to determine the approximate location of the system on the earth's surface.

Pupillometry system 200 addresses many of the shortcomings existing with conventional pupillometers described in the background section. For example, the presently described system 200 can enhance its ability to correctly identify the pupil by identifying the properties of the camera 218 and the radiation source 216. System 200 then references data stored in storage medium 208 properties associated with a variety of different types of camera and radiation sources. System 200 then appropriately modifies the images obtained from camera 218, as well as the intensity of radiation source to bring them into conformance with images obtained under similar conditions from different types of camera or radiation source.

In some cases storage medium 208 may not contain the properties associated with the camera 218 or the radiation source 206. In this case, system 200 measures properties associated with the camera output 216, including overall image brightness, contrast, magnification, focus, and distribution of pixel values over one to three color channels, and based on these measurements system 200 modifies the instructions for pupil identification stored in storage medium 208 and executed by processor 210 to improve detection of the pupil. If camera 218 has the capability to alter image properties prior to their transmission to processor 210, system 200 may adjust camera parameters such that the image is brought into conformance prior to its transmission to processor 210.

In the above case, prior to measuring the image properties of the output of camera 216, system 200 may prompt the user 202 to aim camera 218 at an image or object that will produce a set of conditions that will closely resemble those found when imaging a patient's pupil, such as a printed static image or the pupil of another individual. System 200 will then analyze images obtained from camera 216 to determine the parameters mostly likely to result in successful identification of the pupil in the future and store this information in storage medium 208.

In some cases these measures may still result in failure to accurately detect the pupil. In this case system 200 may display an image of the pupil on display 210 to user 202 and prompt user 202 to evaluate whether the instructions for pupil identification stored in storage medium 208 resulted in successful identification of the pupil. The user 202 may then either input parameters to system 200 that manually change the identification of the pupil, or instruct system 200 to re attempt pupil identification using a different parameters for pupil identification, or instruct system 200 to discard a particular pupil measurement when calculating pupillary measures of change.

After capture of pupil data or calculation of pupillary indices of change, system 200 may apply a unique identifier to the pupil data or the pupillary indices of change and store said data locally on storage medium 208 or transmit said data via communication device 220 to a remote computer system 222. The user 202 may retrieve said data either from the local storage medium 208 or from the remote system 222, or they may allow others to retrieve the data from remote system 222 to review at a future date.

In order to ensure that patient data is not inappropriately captured, stored, or viewed, system 200 may obtain information from the physical positioning system 224. Prior to measuring pupil data, calculating pupillary indices of change, or retrieving said data from a remote system 222 or a local storage medium 208, system 200 may obtain information regarding the device's physical location on earth's surface from the positioning system 224 and use this information to determine whether user 202 is allowed to measure or retrieve pupil data based on their current position.

Various disclosed examples may be implemented using electronic circuitry configured to perform one or more functions. For example, with some embodiments of the invention, the disclosed examples may be implemented using one or more application-specific integrated circuits (ASICs). More typically, however, components of various examples of the invention will be implemented using a programmable computing device executing firmware or software instructions (i.e., computer-readable instructions), or by some combination of purpose-specific electronic circuitry and firmware or software instructions (i.e., computer-readable instructions) executing on a programmable computing device.

Accordingly, FIG. 1 shows one illustrative example of a computer, computer 101, which can be used to implement various embodiments of the invention. Computer 101 may be incorporated within a variety of consumer electronic devices, such as personal media players, cellular phones, smart phones, personal data assistants, global positioning system devices, and the like.

As seen in this figure, computer 101 has a computing unit 103. Computing unit 103 typically includes a processing unit 105 and a system memory 107. Processing unit 105 may be any type of processing device for executing software instructions (i.e., computer-readable instructions), but will conventionally be a microprocessor device. System memory 107 may include both a read-only memory (ROM) 109 and a random access memory (RAM) 111. As will be appreciated by those of ordinary skill in the art, both read-only memory (ROM) 109 and random access memory (RAM) 111 may store software instructions to be executed by processing unit 105.

Processing unit 105 and system memory 107 are connected, either directly or indirectly, through a bus 113 or alternate communication structure to one or more peripheral devices. For example, processing unit 105 or system memory 107 may be directly or indirectly connected to additional memory storage, such as a hard disk drive 117, a removable optical disk drive 119, a removable magnetic disk drive 125, and a flash memory card 127. Processing unit 105 and system memory 107 also may be directly or indirectly connected to one or more input devices 121 and one or more output devices 123. Input devices 121 may include, for example, a keyboard, touch screen, a remote control pad, a pointing device (such as a mouse, touchpad, stylus, trackball, or joystick), a scanner, a camera or a microphone. Output devices 123 may include, for example, a monitor display, an integrated display, television, printer, stereo, or speakers.

Still further, computing unit 103 will be directly or indirectly connected to one or more network interfaces 115 for communicating with a network. This type of network interface 115 is also sometimes referred to as a network adapter or network interface card (NIC). Network interface 115 translates data and control signals from computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 115 may employ any suitable connection agent for connecting to a network, including, for example, a wireless transceiver, a power line adapter, a modem, or an Ethernet connection.

Still further, computing unit 103 will be directly or indirectly connected to one or more devices for ascertaining user position 127. As is known in the art, this will frequently be based on the Global Positioning System or a comparable satellite navigational system.

It should be appreciated that, in addition to the input, output and storage peripheral devices specifically listed above, the computing device may be connected to a variety of other peripheral devices, including some that may perform input, output and storage functions, or some combination thereof.

Computer 101 may be connected to or otherwise include one or more other peripheral devices, such as a telephone. The telephone may be, for example, a wireless "smart phone," such as those featuring the Android or iOS operating systems. As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with computer 101 so that their data maintained may be synchronized.

Of course, still other peripheral devices may be included with or otherwise connected to a computer 101 of the type illustrated in FIG. 1, as is well known in the art. In some cases, a peripheral device may be permanently or semi-permanently connected to computing unit 103. For example, with many computers, computing unit 103, hard disk drive 117, removable optical disk drive 119 and a display are semi-permanently encased in a single housing.

Still other peripheral devices may be removably connected to computer 101, however. Computer 101 may include, for example, one or more communication ports through which a peripheral device can be connected to computing unit 103 (either directly or indirectly through bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, computer 101 may include a wireless data "port," such as a Bluetooth® interface, a Wi-Fi interface, an infrared data port, or the like.

It should be appreciated that a computing device employed according to the various examples of the invention may include more components than computer 101 illustrated in FIG. 1, fewer components than computer 101, or a different combination of components than computer 101. Some implementations of the invention, for example, may employ one or more computing devices that are intended to have a very specific functionality, such as a digital music player or server computer. These computing devices may thus omit unnecessary peripherals, such as removable optical disk drive 119, printers, scanners, external hard drives, etc. Some implementations of the invention may alternately or additionally employ computing devices that are intended to be capable of a wide variety of functions, such as a smartphone, desktop or laptop personal computer. These computing devices may have any combination of peripheral devices or additional components as desired.

Figure 2:
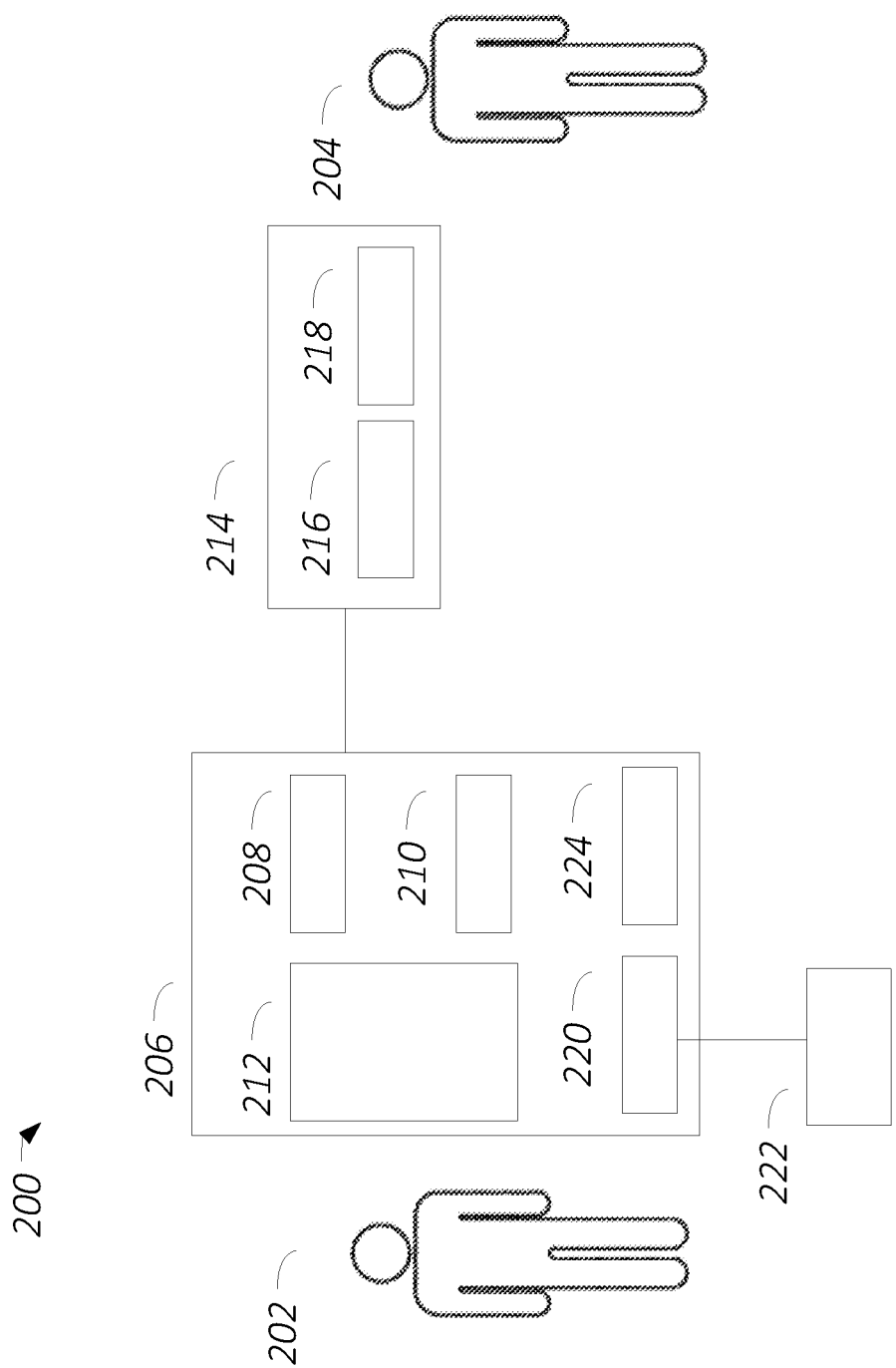
FIG. 2 is a schematic view of a first example pupillometry system including a programmable computing device, such as the example device shown in FIG. 1.

Turning now to FIG. 2, as described above, pupillometry system 200, computer system 206 (non-transitory computer-readable storage medium 208, processor 210, and display 212), positioning device 214 having radiation source 216 and camera 218, communication device 220, and positioning determining system 224. It will be understood that in alternate examples computer system 206 can include any of the additional computer system components described above in reference to computer 101 (shown in FIG. 1). It will be further understood that in other alternate examples the camera and the radiation source can have separate positioning mechanisms and/or can be hand-held.

In existing pupillometers, frequently radiation source 216 is in data communication with computer system 206 and the non-transitory computer-readable instructions include instructions for regulating an "on" state/"off" state and/or an intensity of the radiation source. In some examples, computer system 206 regulates or controls an intensity pattern for the radiation source (e.g., a constant intensity pattern, a fluctuating intensity pattern, etc.). The radiation source is configured to project a desired frequency of radiation (e.g., infrared, visible light, etc.). The radiation source is further configured to project radiation to one or more pupils of the patient. In some examples, the radiation source can project radiation into one or both pupils of the patient. In other examples, the system can include more than one radiation source for separately projecting light into each pupil.

In the present invention, the radiation source may additionally be regulated or controlled by computer system 206 on the basis of analysis of images obtained from camera 218, or on an identification of the type of camera 218 and reference to stored parameters in storage medium 208, or on parameters stored from the performance of a calibration procedure dictated by instructions stored on storage medium 208.

As shown in FIG. 2, in existing pupillometers, frequently camera 218 (e.g., a digital camera) is also in data communication with computer system 206. Computer system 206 can command camera 218 to capture image data and then collect and time-stamp image data captured by the camera. Accordingly, camera 218 is configured to capture image data of one or both of the patient's pupils (e.g., pupils of patient 204). In some examples, the camera captures image data of both pupils of the patient. In other examples, the system can include more than one camera for separately capturing image data of each pupil.

In the present invention, in addition to the above, the camera 218 may be regulated or controlled by computer system 206 on the basis of analysis of images, including distribution of pixel intensity in one or more color channel, obtained from camera 218. This distribution of pixel intensity may be measured for all points in the image, or by a subset of points in a selected portion of the image. Camera 218 may also be regulated or controlled based on an identification of the type of camera 218 and reference to stored parameters in storage medium 208, or on parameters stored from the performance of a calibration procedure dictated by instructions stored on storage medium 208.

In existing pupillometers, the non-transitory computer-readable instructions can further include instructions for collecting image data according to the intensity pattern of the radiation source (e.g., on state, off state, fluctuating intensity, constant intensity, alternating radiation sources, etc.). For example, the computer system can operate the camera to start collecting image data for a specific period of time according to a time when the radiation source is turned on, turned, off, and/or when the intensity is fluctuated. In the present invention the adjustments to the camera 218 and the radiation source 216 may be made prior to starting data collection, or they may be made adjusted continuously during data collection.

In the preferred embodiment of this invention, the radiation source 216, camera 218, input, display, and other components of computing system 206 are all mounted together in a single housing, and the entire monolithic unit is hand held. In alternate examples, the camera and the radiation source(s) can be retained and/or mounted in a different positioning mechanism (e.g., mounted on a stand, mounted on a flexible arm, mounted in a pair of glasses, etc.).

Returning to FIG. 2, in the operation of existing pupillometers, in addition to regulating an "on" state/"off" state and/or an intensity of the radiation source, commanding the camera to capture image data, and collecting and time-stamp image data, computer system 206 is frequently configured to receive commands from operator 202, process the image data, and display the processed image data to the operator.

In the present invention, prior to performing any functions related to data capture, retrieval, or display, system 206 may determine the system's geographic location on the surface of the earth using position determining system 224, and then determine whether to proceed with data capture, retrieval, or display, based upon the identity of operator 202 and authorization information which is stored either on the local storage medium 208 of system 206, or is retrieved from a remote computer system 222 using communication device 220.

In the present invention, prior to data capture, computer system 206 is also capable of prompting operator 202 to calibrate the camera 218 and radiation source 216 by imaging an appropriate test image or test object. Furthermore, after the capture of pupil data, computer system 206 is capable of displaying the captured pupil data along with the location and dimensions of the pupil and/or iris as identified by system 206, and furthermore allowing operator 202 to accept the data, reject the data, or modify the data based on their own interpretation of the image.

Furthermore, in the present invention, after collection of the data, operator 202 may tag the data with a unique identifier, or alternatively system 206 may automatically generate an identifier, and the data can then be transferred to remote computer system 222 using communication device 220. Remote computer system 222 is accessible by multiple users. At a future date operator 202 may then receive this data from remote computer system 222, or receive data from other users who have transferred data to remote computer system 222 and authorized operator 202 to view their data. It is to be understood that the unique identifier generated by system 206 or user 202 may also include information pertaining to the geographic location of the scan on earth's surface, either entered manually by operator 202 or obtained by system 206 from positioning system 224.

A partial example method for operating the pupillometry system, method 300, is shown in FIG. 3, which details the method for calibrating the camera and radiation source prior to beginning the process of data capture. Another partial example method of operations carried out by the computer system to improve the identification of the pupil after data capture, method 400, is shown in FIG. 4.

As depicted in FIG. 3, after a capture is initiated in step 302, in step 304 the system identifies the type of camera and radiation source associated with the system, and attempts to identify suggested parameters for radiation intensity, camera focus, zoom, brightness, contrast, color saturation, and other parameters, and additionally identifies the optimal parameters for the system to identify the pupil and iris in contrast to other structures such as the cornea and skin. At step 306 the system may then determine if the user has performed a calibration operation in the past, and if so, what values for radiation intensity, camera focus, zoom, brightness, contrast, color saturation, and other parameters were stored as a result of the calibration. In the preferred embodiment of this device the results of the calibration would supersede any recommended values based on stored defaults for a given type of camera or radiation source. The system may then optionally prompt the user to perform another calibration.

At step 308 the pupillometer makes further adjustments to lighting and camera parameters based on the measured ambient light, and optionally at step 310 identifies its position on the earth's surface. The position of the device is used to determine whether a data capture is allowed and/or what capture parameters to use. It is to be understood that step 310 may be undertaken not only when the user is attempting to capture data de novo, but also when they are attempting to view or access data that was stored remotely on remote computing system 222. It will also be appreciated that the authorized locations for use may be set by a party other than the current operator in order to maintain data security.

Figure 4:
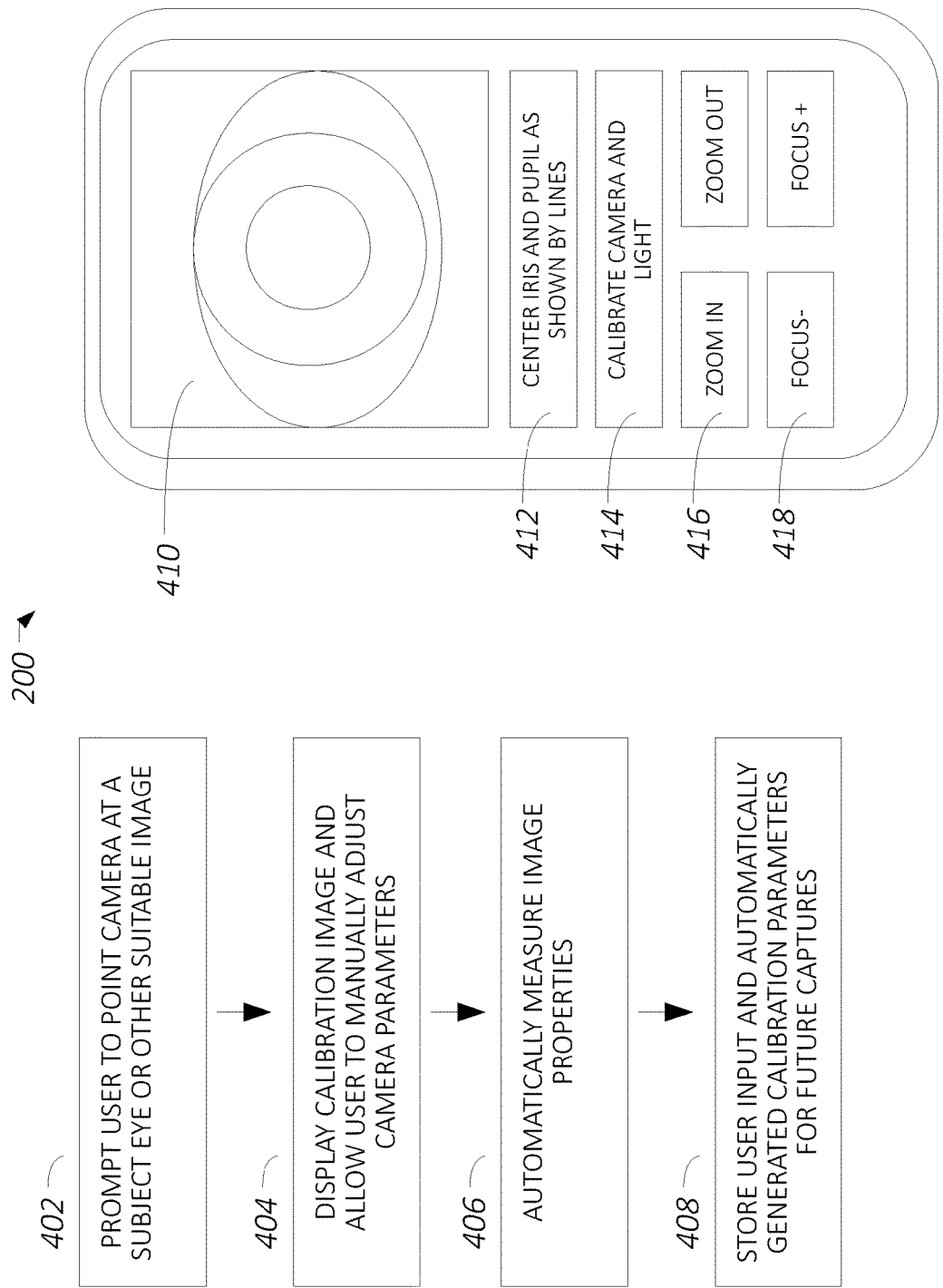
FIG. 4 is an example method of operations for performing the calibration operation of the device, along with an example calibration output screen that can be displayed on the display of the first example pupillometry system shown in FIG. 2.

An example method of operations for performing the above calibration, along with the associated user display, is shown in FIG. 4. In this figure, during steps 402-408 the user is prompted to center the camera on an individual's eye by prompt 412, which can be visualized on display 410. The operator is prompted to adjust the zoom level and focus of the camera until the pupil appears the correct size and focus using inputs 414-418, and then the brightness and contrast of the camera are adjusted until the pixel values associated with the pupil and iris are within the limits used by the pupil detection algorithm. It is to be understood that the system, instead of adjusting the parameters of the camera itself, could adjust the parameters that the processor uses for pupil and iris detection.

The process of capturing data continues in a way common to a variety of existing pupillometers. The radiation source(s) is positioned to project radiation into one or both eyes of the patient and the camera is positioned to capture image data of the pupils from one or both eyes of the patient. Next, the operator sets and/or programs the computer system with the desired parameters for data collection (e.g., radiation pattern, timing for image capture, duration of data collection, pupillary characteristics to be measured, etc.). It will be appreciated that in alternate examples the parameters can be pre-set by the manufacturer (i.e., default settings). In these alternate examples, the operator can manually override and/or adjust the pre-set parameters. The operator then commands the computer system to begin data collection and analysis according to the desired parameters, which may include calibration and camera data identified in steps 304-310.

The preceding steps are common to a number of existing pupillometers. In the present invention, after data capture is complete a method may optionally be employed to improve the quality of pupil data. This method is described in FIG. 5. and illustrated in FIG. 6. After data capture is complete at step 502, the process of data analysis and display begins. In order to perform image data capture, analysis, and display, the non-transitory computer-readable storage medium includes computer-readable instructions for: collecting and time stamping the image data, identifying and measuring the one or more pupils in the image data, processing the image data to produce measurement data of change in the one or more pupillary characteristics, and calculating a standardized output of measurement data for the one or more pupillary characteristics. The present invention details methods for improving identification of the pupils and/or iris. As stated above, one example method of operations for the computer system for identifying the pupils and/or iris, step 504 of FIG. 5, is detailed below.

As depicted in step 504, the computer system identifies ranges of expected red, green, and blue values for pixels associated with the pupil. The expected red, green, and blue values will vary depending on the camera and the type of illumination used, and are obtained using the previously described methods of parameter lookup based on the type of camera and illumination used, and/or based on a calibration performed by the user. The system identifies all pixels within the image that fall within the expected red, green, and blue values, and identifies contiguous or semi contiguous regions of identified pixels that fall within a circle of minimum size. In some embodiments, the system may alter the entire image prior to identification of pixels associated with the pupil.

If the circle surrounding the identified pixels is a size that would be expected for a properly obtained image of the pupil the radius and center of the circle is reported as the radius and center of the pupil. The procedure is then repeated to identify the iris, using color data or sets of color data for differently colored irises that was obtained from stored parameters or previous calibrations. If the reported centers of the iris and pupil differ significantly the procedure is repeated with different color parameters until the two centers are approximately the same.

Figure 5:
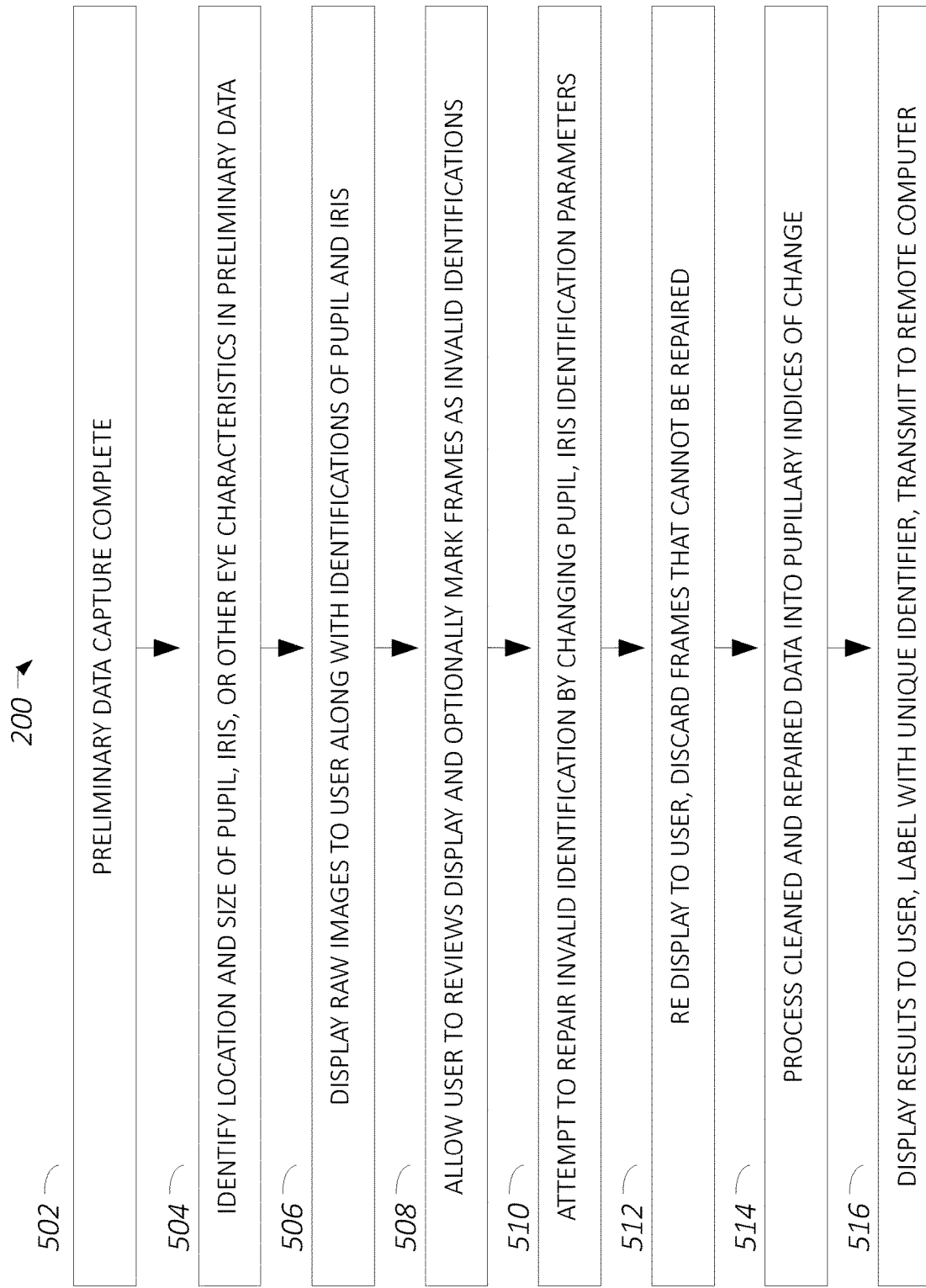
FIG. 5 is a flow diagram of a second example method for use of the example pupillometry system shown in FIG. 2, after data capture is complete. [32]

It will be appreciated by those skilled in the art that while in FIG. 5 the process of identifying the iris and/or pupil does not begin until the data capture is complete and all images have been captured, system 200 could also be configured to perform pupil identification during data capture.

After the automatic detection of the pupil and iris are complete, the preliminary results are displayed in step 506. The operator is given the option to accept or reject the dimensions and the location of the pupil and/or the iris that were identified by the system, and furthermore the operator has the option of requesting that the system re-attempt to identify the pupil using different identification parameters, in steps 508-514.

Figure 6:
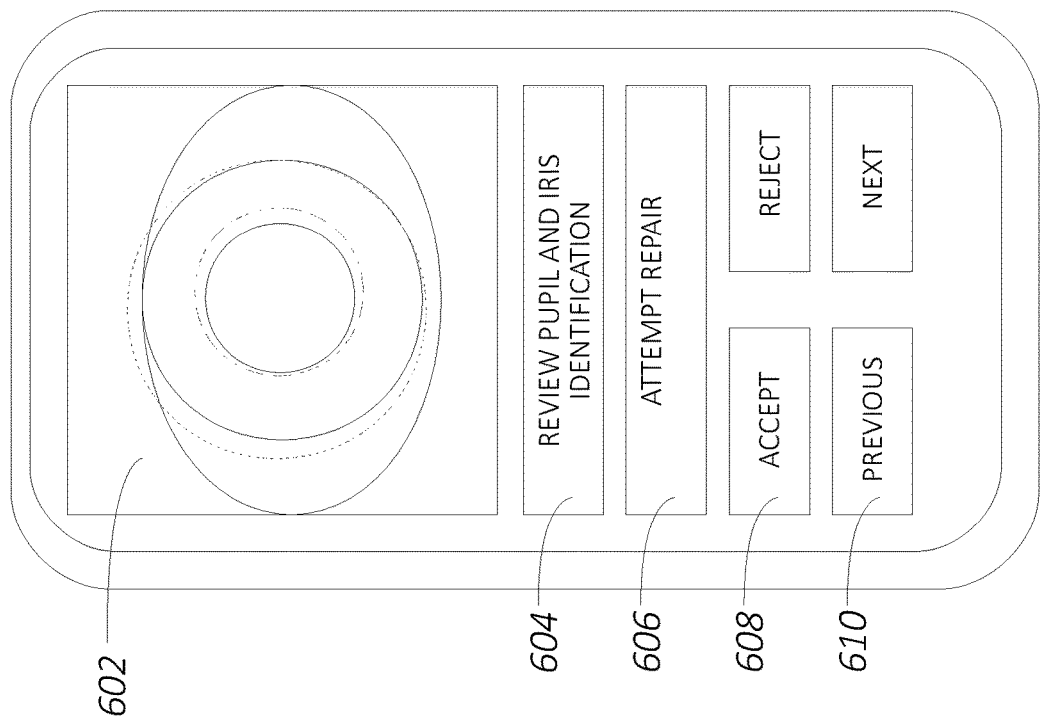
FIG. 6 is an example of the data output screen from that can be displayed on the display of the first example pupillometry system shown in FIG. 2, which allows an operator to review the output of the pupillometer and accept or reject data, as shown in FIG. 5.

An example of this method is shown in FIG. 6. The operator 202 is shown a series of images that were captured by the pupillometer on display 602, along with circles that denote the identifications of the iris and pupil, shown as dashed lines in the figure. The operator is prompted to accept, reject, or attempt repair of this frame using inputs 604-610.

Once the operator has reviewed the pupillary data to their satisfaction, the pupil data may be used to calculate pupillary indices such as pupillary unrest in ambient light, measures of pupillary constriction or dilation, or absolute pupil size. Finally, turning back to FIG. 5 at step 516, the operator and/or another healthcare provider uses the pupillometry data to determine a diagnosis, treatment plan, prognosis, appropriate dose of a medication, etc. for the patient based on the processed pupillometry data. For example, pupillary unrest has been shown to be depressed by opioid pain medications. A patient with depressed pupillary unrest who continues to have pain may be less responsive to further opioid pain medications than other types of pain medication.

Because different operators and/or healthcare providers may provide treatment for a single patient, and because changes in their pupil scans may be helpful in determining diagnosis or treatment plans, it may prove useful for an operator to share scans of a patient with other operators by communicating the scans or data associated with the scans to a central repository. This repository can be accessed by other authorized users, and in turn the operator can access their scans or retrieve his or her own scans.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

CITATION LIST

Patent Literature

U.S. Pat. No. 9,414,745
U.S. Pat. No. 7,083,280
U.S. Pat. No. 3,782,364,
U.S. Pat. No. 5,784,145,
U.S. Pat. No. 7,625,087
U.S. Pat. No. 8,127,882

Non-Patent Literature

AlgometRx pupillographic device, prototype description available at https://atlanticpediatricdeviceconsortium.org/algometrx-pain-and-analgesic-drug-effect-measurement-device
NPi—200, Neuroptics Pupillometer, Product available at www.neuroptics.com.
McAnany, J. Jason, et "iPhone-based pupillometry: a novel approach for assessing the pupillary light reflex." Optometry and Vision Science 95.10 (2018): 953. available at https://www.ncbi.nlm.nih.gov/pmc/articles/PMC6166694/
De Souza, John Kennedy Schettino, et al., An open-source, FireWire camera-based, Labview-controlled image acquisition system for automated, dynamic pupillometry and blink detection, Computer Methods and Programs in Biomedicine, December 2013, pp. 607-623, vol. 112, Issue 3, available at http://www.sciencedirect.com/science/article/pii/S0169260713002460
Maz Warga et al., How do Spontaneous Pupillary Oscillations in Light Relate to Light Intensity?, Vision Research, February 2009, pp. 295-300, vol. 49, Issue 3, available at http://www.sciencedirect.com/science/article/pii/S0042698908004689
Anne-Claire et al., The Relevance of Pupillometry for Evaluation of Analgesia Before Noxious Procedures in the Intensive Care Unit. 2015, available at https://www.ncbi.nlm.nih.gov/pubmed/25993266
B Wilhelm et al., Pupillographic Assessment of Sleepiness in Sleep-Deprived Healthy Subjects, Sleep 12.3, May 1998, pp. 258-265, available at http://www.pubfacts.com/detail/9595604/Pupillographic-assessment-of-sleepiness-in-sleep-deprived-healthy-subjects.

The invention claimed is:

1. A pupillometry system for measuring one or more pupillary characteristics of a patient, comprising:
   at least one camera configured to capture image data of one or more pupils of the patient, wherein the at least one camera has one or more image properties;
   at least one radiation source configured to project radiation to the one or more pupils of the patient, wherein the at least one radiation source has one or more illumination properties; and
   a computer system in data communication with the at least one camera and the at least one radiation source, the computer system including a processor and a non-transitory computer-readable storage medium, the non-transitory computer-readable storage medium having instructions for:
      identifying a camera type of the at least one camera;
      identifying a radiation type of the at least one radiation source;
      accessing a previous calibration of the system to identify optimal image parameters for the camera type and optimal illumination parameters for the radiation type, wherein the optimal image parameters and the optimal illumination parameters result in optimal image data for measuring the one or more pupillary characteristics;
      if no calibration exists, calibrating the system at least in part by:
         based on the camera type and radiation type, identifying recommended image parameters for the at least one camera and recommended illumination parameters for the at least one radiation source, wherein the recommended image parameters and the recommended illumination parameters result in optimal image data for measuring the one or more pupillary characteristics,
         setting the suggested image parameters as the optimal image parameters, and
         setting the suggested illumination parameters as the optimal illumination parameters;
      adjusting the one or more image properties of the at least one camera to match the optimal image parameters;
      adjusting the one or more illumination properties of the least one radiation source to match the optimal illumination properties;
      collecting and time stamping the image data;
      identifying and measuring the one or more pupils in the image data;
      processing the image data to produce measurement data of change in the one or more pupillary characteristics; and
      calculating a standardized output of measurement data for the one or more pupillary characteristics.

2. The system of claim 1, wherein the non-transitory computer-readable storage medium further has instructions for:
   measuring ambient light;
   adjusting the image properties of the at least one camera to compensate for the ambient light; and
   adjusting the illumination properties of the least one radiation source to compensate for the ambient light.

3. The system of claim 1, wherein the optimal image parameters, the optimal illumination parameters, the recommended image parameters, and the recommended illumination parameters are stored on the computer readable storage medium.

4. The pupillometry system of claim 1, wherein the non-transitory computer-readable storage medium has instructions for adjusting the one or more image parameters of the at least one camera and the one or more illumination parameters of the at least one radiation source.

5. The pupillometry system of claim 1, wherein the one or more image properties include one or more of the following: camera focus, zoom, brightness, contrast, color saturation, timing for image capture, and duration of data collection.

6. The pupillometry system of claim 1, wherein the one or more illumination properties include one or more of the following: radiation intensity and radiation patterns.

7. A pupillometry system for measuring one or more pupillary characteristics of a patient, comprising:
at least one camera configured to capture image data of one or more pupils of the patient, wherein the at least one camera has one or more image properties;
at least one radiation source configured to project radiation to the one or more pupils of the patient, wherein the at least one radiation source has one or more illumination properties; and
a first computer system in data communication with the at least one camera and the at least one radiation source, the computer system including a processor and a non-transitory computer-readable storage medium, the non-transitory computer-readable storage medium having instructions for:
accessing optimal image parameters for the at least one camera and optimal illumination parameters for the at least one radiation source, wherein the optimal image parameters and the optimal illumination parameters result in optimal image data for measuring the one or more pupillary characteristics;
adjusting the one or more image properties of the at least one camera to match the optimal image parameters;
adjusting the one or more illumination properties of the least one radiation source to match the optimal illumination properties;
collecting and time stamping the image data;
identifying and measuring the one or more pupils in the image data;
processing the image data to produce measurement data of change in the one or more pupillary characteristics;
calculating a standardized output of measurement data for the one or more pupillary characteristics;
assigning a unique identifier to the standardized output of measurement data; and
transferring the standardized output of measurement data with the unique identifier to a second computing device configured to be accessed by multiple users based on set criteria.

8. The pupillometry system of claim 7, wherein the set criteria includes a physical location of the system on earth's surface as determined by the system.

9. A system for improving quality of captured image data of one or more pupils of a patient, the system comprising:
a display;
a user interface;
at least one processor; and
non-transitory computer-readable storage medium, the non-transitory computer-readable storage medium having instructions for:
accessing captured image data, wherein the captured image data includes captured image properties;
identifying at least one camera used to capture the captured image data;
identifying at least one radiation source used to capture the captured image data;
accessing optimal image properties of the at least one camera and optimal illumination properties of the at least one radiation source, wherein the optimal image parameters and the optimal illumination parameters result in optimal image data for measuring the one or more pupillary characteristics using the captured image data;
adjusting the captured image properties based on the optimal image properties and the optimal illumination properties to produce adjusted imaged data;
identifying the one or more pupils in the adjusted image data;
presenting on the display the identification of the one or more pupils, wherein the user assesses the accuracy of the identification;
receiving input on the user interface one or more of the following:
rejecting and discarding the adjusted image data,
replacing the adjusted image data,
accepting the adjusted image data, or
repeating adjusting the captured image properties using different criteria, identifying the one or more pupils in the adjusted image data, presenting the identification, and receiving input on the user interface;
processing the adjusted image data to produce measurement data of change in one or more pupillary characteristics of the one or more pupils; and
calculating a standardized output of the measurement data for the one or more pupillary characteristics.

10. The system of claim 9, wherein the captured image properties include one or more of the following: image brightness, image contrast, minimum pixel values, distribution of pixel values, and maximum pixel values.

* * * * *